United States Patent [19]

Anapliotis

[11] Patent Number: 4,974,580
[45] Date of Patent: Dec. 4, 1990

[54] ENDOSCOPE PROTECTIVE MEMBER

[75] Inventor: Emmanuel Anapliotis, Berlin, Fed. Rep. of Germany

[73] Assignee: Effner GmbH, Berlin, Fed. Rep. of Germany

[21] Appl. No.: 370,014

[22] Filed: Jun. 23, 1989

[30] Foreign Application Priority Data

Jun. 25, 1988 [DE] Fed. Rep. of Germany ... 8808299[U]

[51] Int. Cl.$^5$ .............................................. A61B 1/00
[52] U.S. Cl. .................................................... 128/4
[58] Field of Search .......................... 128/3, 4, 5, 6, 7

[56] References Cited

U.S. PATENT DOCUMENTS

| | | | |
|---|---|---|---|
| 2,482,971 | 9/1949 | Golson | 128/6 |
| 4,201,199 | 5/1980 | Smith | 128/7 |
| 4,721,097 | 1/1988 | D'Amelio | 128/4 |
| 4,741,326 | 5/1988 | Sidall et al. | 128/4 |
| 4,807,593 | 2/1989 | Ito | 128/4 |
| 4,819,620 | 4/1989 | Okutsu | 128/4 |

FOREIGN PATENT DOCUMENTS 0184778 6/1986 European Pat. Off. .
3716401 11/1987 Fed. Rep. of Germany .

*Primary Examiner*—William H. Grieb
*Attorney, Agent, or Firm*—Spencer & Frank

[57] ABSTRACT

Endoscope equipped with a protective tube including a hollow cylindrical tube body made of plastic and equipped with an optical flat glass which is inserted into a circular, annular recess whose inner diameter becomes smaller toward its end near the object, with the region of reduced inner diameter extending to behind the optical flat glass.

18 Claims, 2 Drawing Sheets

ENDOSCOPE PROTECTIVE MEMBER

BACKGROUND OF THE INVENTION

The invention relates to an endoscope having a protective tube and an optical glass.

Endoscopes are known which can be connected with a commercially available video camera by way of a C-type mount and thus make it possible in dentistry for the patient being treated to view the dental region to be treated on a video monitor in support of the counselling by the treating dentist.

For hygienic reasons, it is necessary to ensure that the endoscope is cleaned between two successive treatments of different patients. Sterilization of the endoscope itself is very complicated and would lead to unjustifiable increases in the cost of the treatment.

SUMMARY OF THE INVENTION

It is the object of the invention to provide an endoscope for which cleaning or, more precisely, the prevention of soiling, is possible in a simple manner.

This is accomplished by the provision of an endoscope having a protective tube equipped with a hollow cylindrical tube body made of plastic and an optical flat glass inserted in a circular ring-shaped recess whose inner diameter becomes smaller toward the end near the object, the reduced inner diameter region extending to behind the optical flat glass.

The invention is based on the realization that a protective tube could be designed which can be re-used after appropriate cleaning or is a disposable article which can be manufactured easily and economically if an optical flat glass element can be introduced in a simple manner at the end on the side of the object so that the optical quality of image observation is ensured. The end on the side of the object where the illuminating light exits is here either provided in a forward viewing arrangement at the frontal face of the tube body or, in an angular viewing arrangement, at the cylindrical wall of the tube body.

In a preferred modification of the invention, the fitting for the optical element is a sleeve of acrylic glass which itself is transparent and thus serves as passage element for the illumination; it need not meet such high optical requirements.

A protective tube of such configuration can be manufactured easily and is thus suitable as an economical, massproduced article.

The illumination field is further improved if the frontal region of the acrylic sleeve at its light exit side is given a frustoconical or lens shaped configuration so that the further outward region, with respect to the light exit surface, is set back.

A non-transparent inner lining of the acrylic sleeve prevents reflections and separates the light serving for illumination from the light received from the object.

According to a preferred modification, endoscopes for angular viewing are equipped with a protective tube in which a sleeve serving as the fitting for an optical flat glass is inserted into the cylindrical wall of the tube body facing the object. The sleeve is here shaped in such a way that it can be firmly pressed into a corresponding recess in the tube body. For this purpose, supporting beads are provided, on the one hand, which engage in blind bores at the exterior of the tube body and, on the other hand, thickened portions are provided which project into the interior of the tube body. The sleeve is preferably made of a weakly elastic plastic or rubber material. For this case of use, the tube body of the protective tube is closed at its front end.

According to an advantageous further feature of the invention, there is provided, in addition to the sleeve equipped with the optical flat glass for the passage of the optical beam path, a second such sleeve for the passage of the illuminating beam path. Both glasses are preferably arranged adjacent to and one behind the other in the axial direction.

The tube is preferably widened at the end opposite the light exit end, i.e. after a conical attachment, it changes into a region of a greater exterior cylindrical diameter which is provided, in particular, with cutouts which permit operation of a knurled ring for sharply focusing the optical system of the endoscope. Moreover, a recess is preferably provided which, toward the end opposite the light exit end, changes into a slit-type opening which permits passage of a glass fiber branch-off for connection of the light source. Since this connection is generally configured as a cylindrical stub, it may serve as a snap-in element for holding the protective tube. Alternatively or in cooperation with this snap-in device, an undercut is preferably provided at the end opposite the light exit end for engagement in a circumferential groove or a corresponding undercut on the optical system of the endoscope and thus also permits the protective tube to be held in a snap-in action.

BRIEF DESCRIPTION OF THE DRAWINGS

Two advantageous embodiments of the invention are illustrated in the drawing figures and will now be described in greater detail. It is shown in.

DETAILED DESCRIPTION OF THE PREFERRED EMBODIMENT

Figure 1:
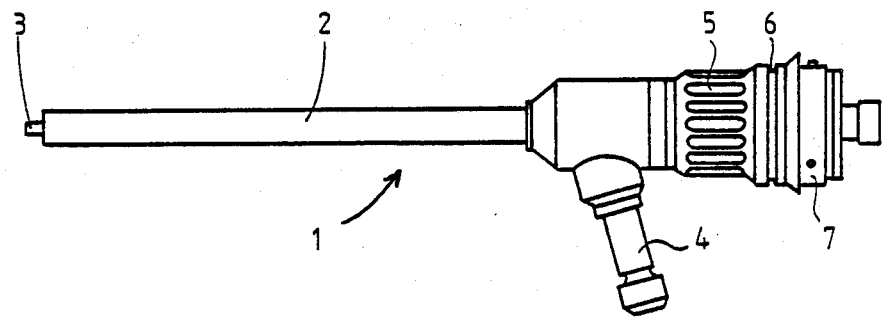
FIG. 1, a forward viewing endoscope for use with a protective tube.

The endoscope 1 for dental applications shown in FIG. 1 comprises an optical system encasing tube 2 which includes in its interior a circular glass fiber arrangement for illumination. At its frontal (light exit) end, an objective lens 3 is provided which projects from the light exit end of optical system encasing tube 2. The opposite end of the endoscope is provided with a laterally projecting connection or stub 4 for the light source and with a knurled ring 5 for sharply focusing the optical system. The knurled ring is followed by a stationary region equipped with an undercut or with a circumferential groove 6 which is followed by a C-mount connection 7 for attachment of a video camera.

Figure 2:
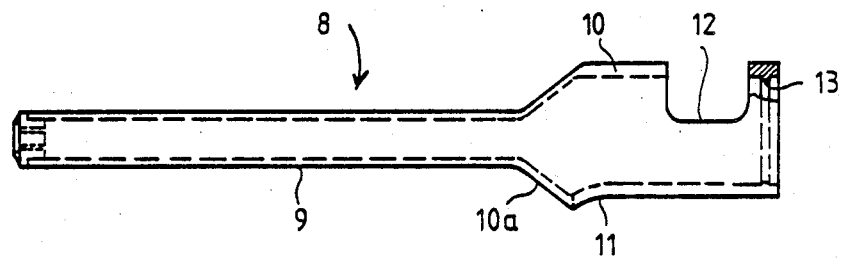
FIG. 2, a protective tube for an endoscope according to FIG. 1.

In the protective tube member 8 shown in FIG. 2, the inner diameter of its hollow cylindrical region 9 is adapted to the outer diameter of the objective lens encasing tube 2 of the endoscope 1. The tube is composed of PVC and is an injection molded component or is produced from a tubular blank by subsequent working.

A region 10 following the region 9 is adapted to the objective lens encasing tube 2 and has a larger cross section than the objective lens encasing tube 2. However, the region 10 is also cylindrical and is oriented coaxially with the region 9. Region 10 is connected with region 9 by way of a frustoconical zone 10a.

Region 10 is provided, with a recess 11 which is adapted to the cross section of the stub 4 for connection of the illumination source. Recess 11 changes from a width adapted to the diameter of the stub 4 to a slit-shaped region of reduced width which extends to the end of the tube opposite the light exit side. Moreover, a recess 12 is provided which, when the protective tube is placed onto the endoscope, is adjacent to the knurled ring 5 so that the knurled ring and thus the focus can be adjusted through this opening.

In a region near recess 12 which is shown in section, there is provided an interior circumferential bead 13 which engages in groove 6 and thus forms a snap-in connection for the protective tube 8. The latter can easily be removed from the endoscope 1 by gripping it with the hand, with the thumb pressing against the connecting element 4 and slightly pushing back the endoscope 1.

Figure 3:
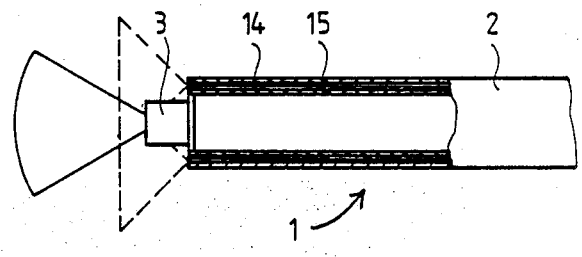
FIG. 3, a sectional view of the front end of the endoscope of FIG. 1 together with the corresponding end of the protective tube of FIG. 2.

FIG. 3 shows the frontal regions of endoscope 1 and protective tube 8 in an enlarged sectional view.

In the sectioned region of objective lens encasing tube 2, a glass fiber arrangement 14 can be seen which is arranged in a circular ring and serves to guide the light. In the interior of glass fiber region 14, there is provided a light-impermeable sleeve 15 for optical decoupling. The objective lens 3 projecting from objective lens encasing tube 2 is arranged in such a manner that, when the protective tube is pushed over it, it reaches an anti-reflection ring 19 provided therein whose inner diameter is adapted to the outer diameter of objective lens 3. This anti-reflection ring 19 is disposed in the interior of an acrylic sleeve 16 which permits the passage of light from the glass fiber arrangement to illuminate the object. When the protective tube 8 is pushed over the endoscope 1, the planar frontal face of the glass fiber arrangement and the inner frontal face of sleeve 16 lie flat on top of one another and thus permit an almost loss-free passage of light, providing optimum object illumination. Acrylic sleeve 16 has a conical annular frontal face which permits refraction of the light exiting from this sleeve to illuminate the object, such that uniform distribution of the illuminating light over the region to be observed is made possible.

A cylindrical ring-shaped recess 18 is provided at the light exit end of the sleeve 15 in front of the anti-reflection ring 19, with its inner diameter being reduced toward the light exit end, i.e. preferably being conical.

However, a step or the like is correspondingly suitable to form a clamping mount for a circular optical flat glass 17 which permits unfalsified observation of the object through objective lens 3. This optical flat glass 17 constitutes part of the protective device and the quality of the optical characteristics must be at a maximum in the region under observation while requirements are lower in the light exit region. Additionally, the protective tube 8 must be opaque in order to prevent the annoying escape of light from the glass fiber arrangement. The illustrated holder for the optical flat glass 17 in the form of the acrylic sleeve 16 thus forms a simple holding element for the optical flat glass 17 as well as simultaneously a light exit element in the transition to the opaque region of the protective tube 8. The thus realized structural optimization permits manufacture from a few costefficient components permitting easy assembly. Acrylic sleeve 16 is preferably pressed into the adjacent region 9 of the tube 8, with grooves or the like provided in adjacent faces of the sleeve 16 and the region 9 improving the mutual connection and simultaneously increasing the resulting tightness of these assembled elements.

Figure 4:
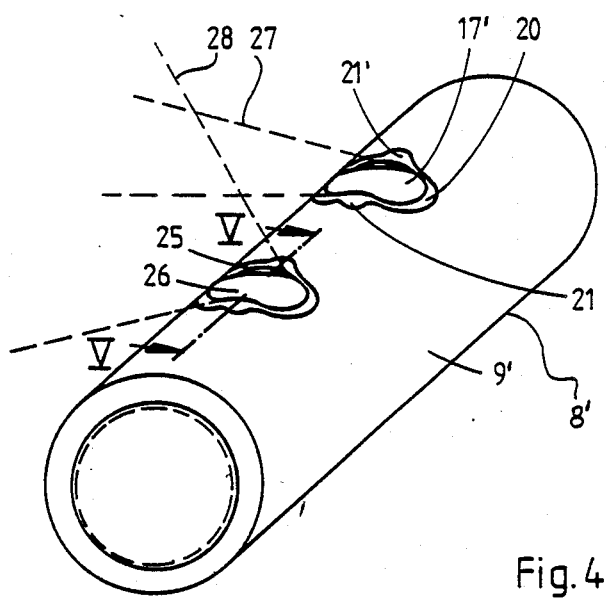
FIG. 4, a perspective view seen obliquely from the top of the front end of a protective tube for an endoscope for angular viewing.
Figure 5:
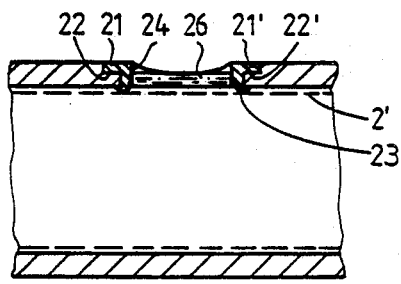
FIG. 5, a sectional view in the direction V—V of FIG. 4.

FIGS. 4 and 5 respectively show an embodiment of an endoscope for angled viewing, in a perspective view and in cross section. In such an endoscope, an optical observation system and illumination exit opening are arranged axially one behind the other. Corresponding to the angle of the optical beam path, an optical flat glass 17' is inserted into the wall of a hollow cylindrical region of a protective tube body 8'. A sleeve 20 which, due to the elasticity inherent in its material, can be pressed into the wall of the tube body 8' to produce a firm seat serves as a mount for the optical flat glass 17'.

Sleeve 20 is provided with two contact beads 21 and 21' which widen in the manner of earlobes in oppositely disposed regions and engage in corresponding blind bores 22 and 22' on the exterior of the tube body 8' and thus prevent sleeve 20 from sliding into the tube body 8'. The ear-like widened portions of the contact beads 21 and 21" serving as blocking elements, therefore extend in the axial direction of the tube body 8' since there the outer surface of the cylindrical tube body 8' has the largest radial distance from the contact surface of the inserted optical flat glass 17' and thus a recess for receiving the contact beads 21 and 21' can have the greatest depth.

In order to also prevent sleeve 20 from sliding outwardly, the latter is provided with an annular undercut 23 in the form of a circumferential sealing lip whose enclosed surface is adapted to the curvature of the inner surface of tube body 9'.

Optical flat glass 17' is pressed into a conical recess 24 of sleeve 20 until it abuts. A second sleeve 25 supports a further optical flat glass 26 which corresponds in shape and size to the light exit surface of the bundled light conducting fibers. Optical flat glass 26 is fastened correspondingly. In order to realize a good overlap for the illuminating light cone 27 and the observation light cone 28, the two sleeves 20 and 25 are disposed in the wall of tube body 8' directly adjacent one another and axially one behind the other.

The sealing lips of the undercuts 23 each rest against the tube body 8' of the endoscope and prevent the transfer of light between the observation beam path and the illumination beam path. This can be seen particularly well for sleeve 21 in the sectional view of FIG. 5 where optical system encasing tube 2' is shown in dashed lines.

The present invention is not limited in its embodiments to the above-described preferred embodiment. Rather, a number of variations are conceivable which take advantage of the described solution even for basically different configurations.

I claim:
1. Endoscope protective member, comprising:
   a hollow cylindrical tube body, said tube body including an end portion which has a circular ring-shaped recess having a reduced inner diameter region at its distal end, and an optical flat glass disposed in said circular ringshaped recess, wherein said reduced inner diameter region is adjacent to a proximal side of said optical flat glass.

2. Endoscope protective member according to claim 1, wherein said optical flat glass which is disposed in said circular ring-shaped recess has a circular cross-sectional outline.

3. Endoscope protective member according to claim 1, wherein an acrylic sleeve forms said end portion of said tube body and includes said circular ring-shaped recess of said tube body, wherein said acrylic sleeve is partially received within a hollow tubular portion of said tube body and has a frontal face which is capable of transmitting light into the interior of said tube body.

4. Endoscope protective member according to claim 3, wherein said acrylic sleeve has a distal end face of which has a frustoconical face.

5. Endoscope protective member to claim 3, wherein said acrylic sleeve includes an inner portion which forms a cylindrical interior surface of the acrylic sleeve and which is impermeable to light.

6. Endoscope protective member to claim 5, wherein said inner portion of said acrylic sleeve which is light impermeable is a metal, sleeve-shaped anti-reflection element.

7. Endoscope protective member according to claim 1, wherein the hollow tubular portion of said tube body includes a tubular wall, and wherein said end portion of said tube body includes a sleeve which has said reduced inner diameter region, said tubular wall having an opening, and said sleeve is received within said opening in said tubular wall.

8. Endoscope protective member according to claim 7, wherein said sleeve is composed of an elastic material.

9. Endoscope protective member according to claim 7, wherein said sleeve includes at least one contact bead which is received within a countersunk recess which is adjacent said opening in said tubular wall passes behind a blind bore on an exterior portion of said tube body, and said contact bead has a greater extent in the longitudinal direction of said tube body than in a circumferential direction of said tube body.

10. Endoscope protective member according to claim 7, wherein said sleeve includes a region which extends into the interior of said tube body, said region of said sleeve including a lip, said lip forming an optical seal between said sleeve and said tubular wall of said tube body, said lip having an outer diameter which exceeds the diameter of said opening in said tubular wall of said tube body so as to retain said sleeve in said opening.

11. Endoscope protective member according to claim 7, wherein a further opening is disposed in said tubular wall, and further comprising a second sleeve disposed in said further opening.

12. Endoscope protective member according to claim 1, wherein a proximal end of said tube body is wider than a central portion of said tube body.

13. Endoscope protective member according to claim 1, wherein said proximal end of said tube body has at least a first recess.

14. Endoscope protective member according to claim 13, further comprising a second recess disposed in said protective tube, said second recess being arranged diagonally opposite each other along said tube body.

15. Endoscope protective member according to claim 13, wherein said first recess is a slit-shaped recess which is disposed in said tube body starting at said proximal end of said protective tube, said protective tube including a region which is widened in a direction which is transverse to the longitudinal extent of said slit-shaped recess.

16. Endoscope protective member according to claim 1, wherein the proximal end of said tube body includes an annularly circumferential, raised region having an undercut.

17. Endoscope protective member according to claim 1, further comprising an anti-reflection ring disposed within a central interior portion of said tube body which is adapted to receive an object lens of an endoscope, in which the anti-reflection ring has an inner diameter which is greater than that of an outer diameter of the object lens of the endoscope, said anti-reflection ring being adapted to closely receive the outer diameter of the object lens of the endoscope.

18. An endoscope in combination with a protective tube, the endoscope comprising an optical system and an optical system encasing tube which surrounds said optical system, said optical system including an objective lens disposed at a distal end of said encasing tube;

said protective tube including a hollow cylindrical portion adapted to receive said encasing tube and said objective lens, a sleeve supported at the distal end of said hollow cylindrical portion, said sleeve supporting an optical glass, and wherein said sleeve is adapted to receive said objective lens.

* * * * *

UNITED STATES PATENT AND TRADEMARK OFFICE
CERTIFICATE OF CORRECTION

PATENT NO. : 4,974,580

DATED : December 4, 1990

INVENTOR(S) : Emmanuel Anapliotis

Figure 2A:
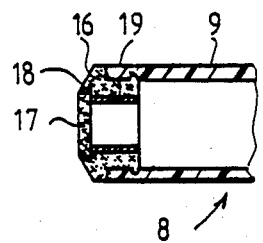

It is certified that error appears in the above-identified patent and that said Letters Patent is hereby corrected as shown below:

Column 2,

After "to FIG. 1;" in line 38, insert the following paragraph:

--FIG. 2a, an enlarged sectional view of a detail of FIG. 2;--.

Line 40, change "scope of FIG. 1 together with the corresponding end of" to --scope of FIG. 1;-- (semicolon).

Line 41, delete "the protective tube of FIG. 2;".

Line 63, change "member 8 shown in FIG. 2" to --member 8 shown in FIGS. 2 and 2a--.

Column 3,

Line 25, change "endoscope 1 and" to --endoscope 1.--.

UNITED STATES PATENT AND TRADEMARK OFFICE
CERTIFICATE OF CORRECTION

PATENT NO.   : 4,974,580

DATED        : December 4, 1990

INVENTOR(S)  : Emmanuel Anapliotis

It is certified that error appears in the above-identified patent and that said Letters Patent is hereby corrected as shown below:

Col. 3, line 26, delete "protective tube 8 in an enlarged sectional view.".

Signed and Sealed this

Twenty-seventh Day of October, 1992

Attest:

DOUGLAS B. COMER

Attesting Officer

Acting Commissioner of Patents and Trademarks